United States Patent [19]
Brull et al.

[11] 3,966,326
[45] June 29, 1976

[54] METHOD AND APPARATUS FOR INDICATING OR MEASURING CONTACT DISTRIBUTION OVER A SURFACE

[75] Inventors: Maurice A. Brull, Tel Aviv; Mircea Arcan, Ramat Hasharon, both of Israel

[73] Assignee: Ramot University Authority for Applied Research & Industrial Development Ltd., Tel Aviv, Israel

[22] Filed: Mar. 17, 1975

[21] Appl. No.: 559,240

[30] Foreign Application Priority Data
Mar. 29, 1974  Israel.................................. 44525

[52] U.S. Cl............................... 356/114; 350/149; 356/35
[51] Int. Cl.²......................................... G01B 11/18
[58] Field of Search ................. 356/33, 35, 71, 114; 350/149

[56] References Cited
UNITED STATES PATENTS

| | | |
|---|---|---|
| 2,625,850 | 1/1953 | Stanton.................................. 356/33 |
| 3,034,395 | 5/1962 | Zandman............................. 350/149 |
| 3,082,664 | 3/1963 | Acloque................................. 356/35 |
| 3,096,388 | 7/1963 | Davenport............................. 356/33 |

*Primary Examiner*—John K. Corbin
*Assistant Examiner*—Richard A. Rosenberger
*Attorney, Agent, or Firm*—Benjamin J. Barish

[57] ABSTRACT

A method and apparatus are described for indicating or measuring contact pressure distribution over a surface, in which method and apparatus, a pressure-transmitting member having a plurality of point-contact projections is used to transmit the contact pressure, in the form of a plurality of localized points, to a photoelastic member. The photoelastic member is one whose optical properties are changed when the member is subjected to pressure, and the changes in optical properties are optically displayed by directing polarized light onto the photoelastic member to produce interference patterns at the localized points of contact pressure.

15 Claims, 5 Drawing Figures

METHOD AND APPARATUS FOR INDICATING OR MEASURING CONTACT DISTRIBUTION OVER A SURFACE

BACKGROUND OF THE INVENTION

The present invention relates to a method and apparatus for indicating or measuring contact pressure distribution over a surface.

Contact pressure distribution measurements are now made by electronic or mechanical pressure transducers, but these have a number of drawbacks. For example, many of them are large and bulky, and even when they are miniaturized, it is still difficult to adapt them for use in a limited space because of their electrical and mechanical connections. In addition, the introduction of the transducers produces local stiffness changes in the contact surface which may affect the measurements. Further, the known electronic and mechanical pressure transducers generally do not permit simultaneous measurements of the pressure distribution over a complete large surface. Finally, such known systems are generally very costly to produce, and moreover they require a high level of technical personnel to operate and maintain them.

SUMMARY OF THE INVENTION

An object of the present invention is to provide a new method and apparatus, having advantages in the above respects, for indicating or measuring contact pressure distribution.

The method and apparatus of the present invention indicate or measure the contact pressure distribution by a new interferometric technique which permits the observation and the photographic recording, under both static and dynamic conditions, of the contact pressure distribution over the whole contact surface on which the pressure is applied. This new technique thus allows the examination of the entire contact pressure distribution field, and moreover, it permits this to be done by a relatively simple and inexpensive apparatus. The invention thus substantially eliminates the above mentioned drawbacks of the presently used electronic or mechanical pressure transducers.

Photoelastic materials which heretofore have been used for indicating or measuring stresses in parts and structures have the property of changing their optical properties, namely their index of refraction, when subjected to stresses. The change in optical properties is dependent on the degree of stresses developed. A polarized light wave passing through the stressed material splits into separate beams, each vibrating along a principal stress direction, and each travelling at a different speed. A "phase shift" between these two beams is produced by the stresses, resulting in an optical interference pattern which can be displayed and recorded. Thus, when such an optically sensitive material is subjected to forces and viewed under polarized light, the resulting stresses are seen as colored intereference patterns which can be interpreted to indicate the overall stress distribution and to provide accurate measurements of the stress directions and magnitudes.

Heretofore, photoelectric sheets have been used for measuring in-plane stresses, i.e. stresses produced in the material by forces substantially co-planar to the sheet itself. For example, they are frequently used to measure stress distribution in models of parts and structures such as gears, engine blocks, pressure vessels, and the like to indicate, e.g., the location of stress concentrations.

Generally speaking, the present invention utilizes these photoelastic materials for indicating or measuring contact pressure distribution over a surface, by providing means for converting the pressures perpendicular to the material into "in-plane" stresses coplanar to the material. This is effected by the use of a pressure-transmitting member having one surface for receiving the contact pressure to be measured, the opposite surface including a plurality of point-contact projections effective to transmit the contact pressure in the form of a plurality of localized points to the photoelastic member. The photoelastic member is supported by a relatively rigid transparent plate, e.g., of glass, and is constrained between same and the pressure-transmitting member so as to convert the perpendicular pressures into in-plane stresses. The changes in optical properties resulting by the in-plane stresses are clearly visible and provide an indication of the distribution of the surface contact pressure applied to the pressure-transmitting member.

The method and apparatus of the invention are particularly useful in providing accurate measurements of contact pressure distribution, both static and dynamic, in biomechanical applications, for example, such as when a person is standing, sitting, or relining on his back. One such application is in measuring the pressure distribution between the human foot and the ground under static conditions (i.e., while the person is standing) and under dynamic conditions (i.e., while he is walking). Such measurements are extremely helpful in the diagnosis of many types of foot defects. This technique can also be used to give quantitative information needed for the systematic design of all types of orthopaedic appliance, ranging from corrective sole members to artifical limbs and braces.

The invention may also be used in designing different types of seating, bedding, and support protheses for sitting or reclining postures.

Since the invention is particularly useful for measuring pressure distributions between the human foot and the ground, it is described below with respect to that application, but it will be appreciated that it could advantageously be used in many other applications as well, some of which are mentioned below.

BRIEF DESCRIPTION OF THE DRAWINGS

The invention is herein described, somewhat diagrammatically and by way of example only, with reference to the accompanying drawings, wherein.

DESCRIPTION OF THE PREFERRED EMBODIMENT

Figure 3:
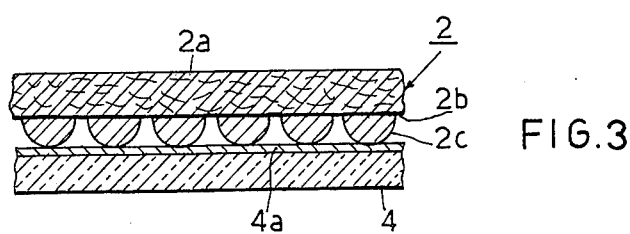
FIG. 3 is an enlarged fragmentary view showing the pressure-transmitting member and the photoelastic member in section.

The apparatus illustrated in the drawings is particularly useful for measuring the pressure distribution over the bottom surface of a person's foot. This pressure distribution is illustrated (in FIG. 1) by the diagram generally designated PD. The pressure is applied to the upper face 2a (FIG. 3) of a flexible pressure-transmitting member 2. The opposite face of pressure-transmitting member 2 is indicated at 2b and is formed with a plurality of point-contact projections 2c.

Figure 2:
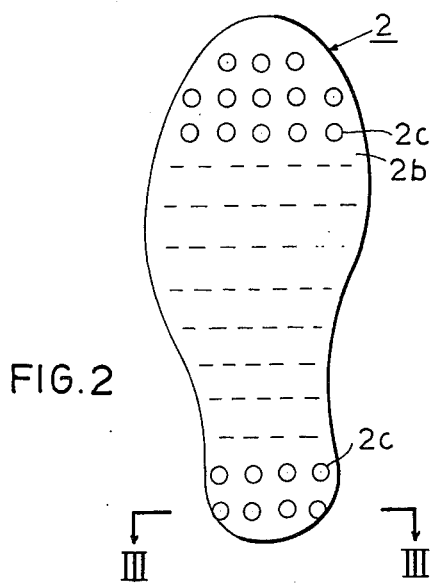
FIG. 2 is a plan view of the pressure-transmitting member used in the apparatus of FIG. 1, this figure illustrating the face of the pressure-transmitting member in contact with the photoelastic member.

In the described embodiment of the invention, the pressure-transmitting member 2 is in the shape of the sole of a shoe, as shown in FIG. 2.

Underlying the pressure transmitting member 2 is a photoelastic member 4 in the form of a sheet carrying a light-reflecting coating 4a on its upper face in contact with projections 2c of the pressure transmitting member 2. Except for light-reflecting coating 4a, the photoelastic member 4 is transparent.

Underlying the photoelastic member 4 is a circular light-polarizer 6 for polarizing the light directed to, and returning from, the photoelastic member.

The pressure-transmitting member 2, photoelastic member 4, and light polarizer 6, are all supported on a relatively rigid transparent plate 8, such as glass or a transparent plastic, the latter being more easily formable and enabling the plate to be curved if desired.

Underlying transparent plate 8 is a semi-reflector or beam-splitter 10 which permits light from a light source 12 to pass therethrough to the photoelastic member 4. Beam-splitter 10 reflects the light from the photoelastic member to display the interference patterns produced thereby, for visual observation or for recording by a camera 14.

Figure 1:
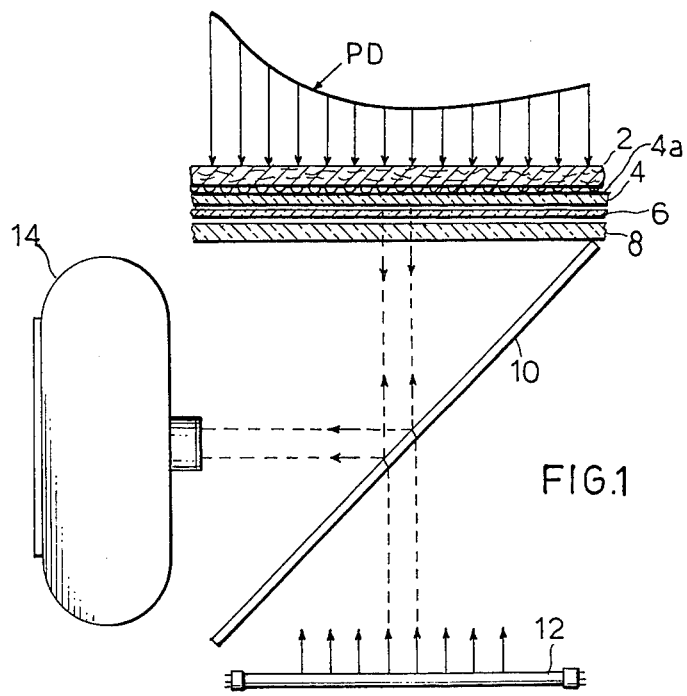
FIG. 1 is a diagram illustrating one form of apparatus constructed in accordance with the invention.

The apparatus illustrated in FIG. 1 operates as follows: The person being examined stands on top of the sole-shaped pressure-transmitting member 2 with the sole of his foot in contact with the upper face 2a of that member. His weight is thus distributed over the complete surface 2a of member 2, as indicated by the pressure diagram PD of FIG. 1.

The projections 2c on the lower face 2b of the pressure-transmitting member, being in contact with the upper face 4a of the photoelastic member 4, transmit the pressure to the latter member in the form of localized pressure spots or points at the points of contact of the projections with surface 4a of the photoelastic member 4. Since the photoelastic member is constrained between the pressure-transmitting member and the rigid transparent plate 8, the localized pressure points are converted to "in-plane" stresses in the photoelastic member at each pressure spot.

The light from source 12 passes through the semi-reflecting mirror or beam-splitter 10, the supporting transparent plate 8, polarizer 6, and photoelastic member 4, and is reflected by reflecting coating 4a on the latter member back through the photoelastic member, polarizer and transparent supporting plate. It is then reflected by beam-splitter 10 for recording by camera 14 or for visual observation.

The interference patterns produced in the photoelastic member 4 and visually observed or recorded by camera 14 will thus be an indication or measurement of the contact pressure distribution over surface 2a of the pressure-transmitting member 2.

The point-contact projections 2c on the underface 2b of the pressure-transmitting member 2, which convert the perpendicular pressures applied to surface 2a into in-plane stresses in the photoelastic member 4, may take a number of different shapes and may be arranged in a number of different patterns, according to the specific application. In the application illustrated in FIGS. 1–3, they are of parabolic shape, having a projection of 4 mm, with 10 mm spaceing between centre points.

In other applications however, they may take other shapes, for example, spherical, or conical. Where high pressures are involved, their surfaces in contact with the photoelastic member usually would be more rounded, and their spaceings would be greater; whereas in lower pressure measurements, their surfaces in contact with the photoelastic member may be more pointed and with closer spaceings.

An example of a photoelastic member 4 which may be used is a sheet of commercially-available epoxy or polycarbonate photoelastic material of a thickness of 3 mm, and an example of a flexible-pressure-transmitting member 2 that may be used is flexible leather of a thickness of 3 mm with the projections 2c being 4 mm and made of rigid plastic such as methacrylate resin or of metal.

Figure 4:
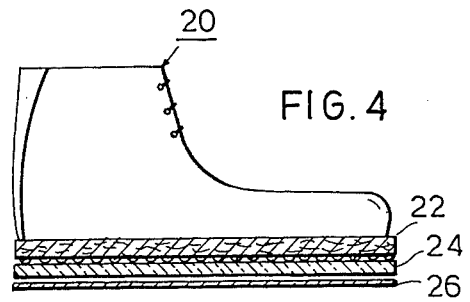
FIG. 4 illustrates the pressure-transmitting member incorporated into the sole of a shoe.

The pressure-transmitting member may also be built into an examining shoe. This is shown in FIG. 4, wherein the examining shoe 20 includes the pressure-transmitting member 22 as the sole of the shoe. Thus, the person being examined need only insert his foot into the shoe and step on the photoelastic member 24, the latter member together with the polarizer 26 being supported on the rigid transparent plate (8 in FIG. 1, not shown in FIG. 4), whereupon the pressure distribution pattern over the bottom surface of the shoe can be visually observed or recorded as in the arrangement of FIGS. 1–3.

Preferably, the contact pressure distribution would be examined simultaneously for both feet of the person, by his wearing two shoes 20.

The apparatus can be used for measuring not only the pressure distribution under static conditions (i.e., while the user is standing), but also under dynamic conditions, (while he is walking). Particularly for the latter application, it would be possible also to include the photoelastic member 24 and the polarizer 26 into the shoe, as a sandwich with member 22, to constitute the sole of the shoe. The user would then need only walk on the transparent supporting plate, and the contact pressure distribution patterns could be observed or recorded during these dynamic conditions. When recording these patterns, a movie camera would be used instead of a still camera.

The sensitivity of the photoelastic member can easily be adapted to any particular application by using material of the appropriate stiffness and thickness. In addition a sandwich construction can be used to produce the appropriate stiffness and/or thickness by including the photoelastic sheet and another transparent elastic sheet, with the polarizer in between.

Figure 5:
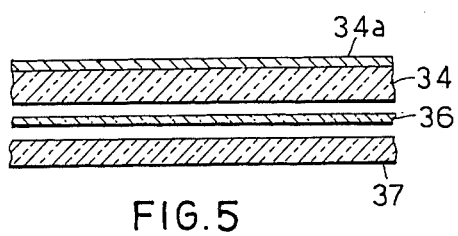
FIG. 5 illustrates a sandwich construction including two photoelastic members sandwiching the polarizer, which construction can be used in the apparatus.

Such a sandwich construction is illustrated in FIG. 5, wherein the polarizer 36 is sandwiched between the photoelastic sheet 34 (on the face opposite the reflector 34a) and another transparent elastic sheet 37. The photoelastic properties of the latter sheet are not utilized but nevertheless it is preferred to use the same material as sheet 34.

In all the foregoing constructions, there should be slip between the various members, except the light-reflector which is preferably a coating or a thin sheet. Slip can be easily provided by dusting lightly with talcum powder.

The pressure-transmitting and photoelastic members, particularly when the sandwich construction is used, may be curved to conform to a curved surface, such as the arch of a foot, the pressure distribution over which is to be measured.

While the above described method and apparatus can be very helpful for diagnosing many types of foot defects and for providing data in preparing orthopaedic shoes to cure these defects, the invention may be used in many other applications. The main characteristics of every application are: the specific purpose including the shape and area on which the pressure has to be applied and measured; the range of pressure to be measured; and the sensitivity of the photoelastic member or sandwich and the shape of the point-contact projections designed according to the above requirements. Such applications may include, for instance, in biomechanics and ergonomics: analysis of the human hand capabilities; human body weight distribution; man-machine contact problems; and man-ground contact in the working process or in sport. In engineering mechanics, they may include, for instance: ground contact pressure of automobile tires or of airplanes during landing; and ground contact pressure of snowmobiles, sledges or skis.

It will be appreciated the light source could be located adjacent to the camera, in which case the semi-reflector or beam-splitter 10 would be a simple mirror.

It is also contemplated that the light source could be a laser, and that electro-optical or holographic techniques could be used to carry out the measurements.

Many other variations, modifications and applications of the invention will be apparent.

What is claimed is:

1. A method for indicating the contact pressure distribution over a surface, comprising the steps: transmitting the contact pressure to be indicated to a photoelastic member through a pressure-transmitting member having a plurality of point-contact projections effective to transmit said contact pressure to the photoelastic member in the form of a plurality of localized points, the photoelastic member being one whose optical properties are changed when the member is subjected to pressure; and optically displaying the changes in the optical properties of the photoelastic member.

2. The method as defined in claim 1, wherein the changes in the optical properties of the photoelastic member are displayed by directing polarized light onto the photoelastic member to produce interference patterns at the localized points of contact pressure.

3. Apparatus for indicating the contact pressure distribution over a surface, comprising: a photoelastic member whose optical properties are changed when the member is subjected to pressure; a pressure-transmitting member having one surface adapted to receive the contact pressure, the opposite surface including a plurality of point-contact projections effective to transmit the contact pressure in the form of a plurality of localized pressure points to the photoelastic member; and means for optically displaying the changes in the optical properties of the photoelastic member.

4. Apparatus as defined in claim 3, wherein said optically-displaying means comprises a light-source directing light to the photoelastic member, and a circular polarizer polarizing the light from the source received by the photoelastic member.

5. Apparatus as defined in claim 4, further including a light reflector on the side of the photoelastic member facing the projections, the opposite side of the photoelastic member facing the light source and the polarizer.

6. Apparatus as defined in claim 5, wherein the light reflector is in the form of a thin sheet or coating on the face of the photoelastic member facing said projections.

7. Apparatus as defined in claim 5, wherein said photoelastic member and light polarizer are supported on one face of a rigid transparent plate, the light source being disposed on the opposite side of the rigid transparent plate.

8. Apparatus as defined in claim 7, further including a transparent elastic sheet between the polarizer and the rigid transparent plate, said transparent elastic sheet forming a sandwich with the photoelastic member with the polarizer inbetween.

9. Apparatus as defined in claim 8, wherein said transparent elastic sheet is of the same material as the photoelastic member.

10. Apparatus as defined in claim 7, further including a camera for photographing the light reflected from said reflector through the photoelastic member, polarizer and transparent supporting plate.

11. Apparatus as defined in claim 3, wherein said point-contact projections carried by the pressure-transmitting member have rounded tips in contact with the photoelastic member.

12. Apparatus as defined in claim 3, wherein the pressure-transmitting member is a thin, flexible sheet.

13. Apparatus as defined in claim 3, wherein said pressure-transmitting member is in the shape of the sole of a shoe for measuring the pressure distribution of a person's weight over the soles of his feet.

14. Apparatus as defined in claim 13, wherein said sole-shaped pressure-transmitting member is built into and constitutes a part of the sole of the shoe.

15. Apparatus as defined in claim 3, wherein said photoelastic member, polarizer, and pressure-transmitting member are formed as one unit.

* * * * *